United States Patent
Nova et al.

(10) Patent No.: US 7,120,488 B2
(45) Date of Patent: Oct. 10, 2006

(54) THERAPY-DELIVERING PORTABLE MEDICAL DEVICE CAPABLE OF TRIGGERING AND COMMUNICATING WITH AN ALARM SYSTEM

(75) Inventors: Richard C. Nova, Kirkland, WA (US); Shawn R. Bertagnole, Lake Stevens, WA (US); William E. Saltzstein, Woodinville, WA (US); Henry Eide, Ferndale, WA (US); Tarek Z. El-Abbady, Redmond, WA (US)

(73) Assignee: MedTronic Physio-Control Manufacturing Corp., Redmond, WA (US)

( * ) Notice: Subject to any disclaimer, the term of this patent is extended or adjusted under 35 U.S.C. 154(b) by 337 days.

(21) Appl. No.: 10/141,574

(22) Filed: May 7, 2002

(65) Prior Publication Data

US 2003/0212311 A1 Nov. 13, 2003

(51) Int. Cl.
*A61N 1/08* (2006.01)
(52) U.S. Cl. .............................. 607/2; 607/60; 128/903; 128/904
(58) Field of Classification Search .................... 607/5, 607/32, 60; 128/903, 904
See application file for complete search history.

(56) References Cited

U.S. PATENT DOCUMENTS

| | | | |
|---|---|---|---|
| 3,553,383 A | 1/1971 | Rochtus | 379/217.01 |
| 3,611,361 A | 10/1971 | Gallichotte et al. | 340/505 |
| 3,632,879 A | 1/1972 | Freisinger | 379/40 |
| 3,634,846 A | 1/1972 | Fogiel | 340/521 |
| 3,662,111 A | 5/1972 | Rubinstein | 379/38 |
| 3,843,841 A | 10/1974 | Rubinstein | 379/38 |
| 3,883,695 A | 5/1975 | Bickel et al. | 379/40 |
| 3,914,692 A | 10/1975 | Seaborn, Jr. | 455/521 |
| 3,989,900 A | 11/1976 | Dibner | 379/50 |
| 4,011,409 A | 3/1977 | Conrad | 379/38 |
| 4,064,368 A | 12/1977 | Dibner | 379/38 |
| 4,141,006 A | 2/1979 | Braxton | 379/40 |
| 4,259,548 A | 3/1981 | Fahey et al. | 379/38 |
| 4,303,801 A | 12/1981 | Anderson et al. | 379/47 |
| 4,338,493 A | 7/1982 | Stenhuis et al. | 379/38 |
| 4,417,100 A | 11/1983 | Carlson et al. | 379/51 |
| 4,577,182 A | 3/1986 | Millsap et al. | 340/539.17 |
| 4,635,639 A | 1/1987 | Hakala et al. | 607/4 |
| 4,654,640 A | 3/1987 | Carll et al. | 340/568.2 |
| RE32,856 E | 2/1989 | Millsap et al. | 340/539.19 |
| 4,829,285 A | 5/1989 | Brand et al. | 340/573.1 |
| 4,887,291 A | 12/1989 | Stillwell | 379/39 |
| D313,362 S | 1/1991 | Reich et al. | D10/106 |
| 5,131,019 A | 7/1992 | Sheffer et al. | 379/39 |
| 5,144,294 A | 9/1992 | Alonzi et al. | 340/825.49 |

(Continued)

*Primary Examiner*—Carl Layno
(74) *Attorney, Agent, or Firm*—Mary Yawney Redman

(57) ABSTRACT

A therapy-delivering, portable medical device (200) capable of triggering and/or communicating with an alarm system (100), as well as a related system and method therefor. The portable medical device (200) is configured to establish a communication link (107) with an alarm system (100) such as a residential or business alarm, upon the occurrence of a triggering event. Triggering events may be related to the use, operation or deployment of the portable medical device (200) in an emergency situation, or they may be for service, status or maintenance purposes, e.g., to report device failures, system checks, etc. The portable medical device (200) is configured to deliver therapy to a patient, wherein the therapy delivered to the patient may be any or combination of medial therapies, e.g., defibrillation, drugs, etc., for any one or combination of medical applications, such as stroke, cardiac arrest, diabetic shock, etc.

101 Claims, 9 Drawing Sheets

U.S. PATENT DOCUMENTS

| | | | |
|---|---|---|---|
| 5,159,317 A | 10/1992 | Brav | 340/574 |
| 5,173,932 A | 12/1992 | Johansson et al. | 379/40 |
| 5,228,449 A | 7/1993 | Christ et al. | 600/504 |
| 5,283,816 A | 2/1994 | Gomez Diaz | 379/40 |
| 5,305,370 A | 4/1994 | Kearns et al. | 379/45 |
| 5,319,355 A * | 6/1994 | Russek | 340/573.1 |
| 5,388,144 A | 2/1995 | Nichols | 379/40 |
| 5,402,466 A | 3/1995 | Delahanty | 379/44 |
| 5,438,607 A | 8/1995 | Przygoda, Jr. et al. | 379/38 |
| 5,549,115 A | 8/1996 | Morgan et al. | 600/508 |
| 5,549,659 A | 8/1996 | Johansen et al. | 607/60 |
| 5,555,286 A | 9/1996 | Tendler | 455/404.2 |
| 5,566,339 A | 10/1996 | Perholtz et al. | 713/340 |
| 5,593,426 A | 1/1997 | Morgan et al. | 607/5 |
| 5,642,397 A | 6/1997 | Agbaje-Anozie | 370/313 |
| 5,673,304 A | 9/1997 | Connor et al. | 379/45 |
| 5,674,252 A | 10/1997 | Morgan et al. | 607/5 |
| 5,680,864 A | 10/1997 | Morgan et al. | 600/518 |
| 5,683,423 A | 11/1997 | Post | 607/5 |
| 5,683,432 A | 11/1997 | Goedeke et al. | 607/5 |
| 5,694,452 A | 12/1997 | Bertolet | 379/51 |
| 5,712,619 A | 1/1998 | Simkin | 340/539.13 |
| 5,731,757 A | 3/1998 | Layson, Jr. | 340/573.1 |
| 5,742,233 A | 4/1998 | Hoffman et al. | 340/573.1 |
| 5,745,849 A | 4/1998 | Britton | 455/404.1 |
| 5,749,902 A | 5/1998 | Olson et al. | 607/5 |
| 5,749,913 A | 5/1998 | Cole | 607/59 |
| 5,752,976 A | 5/1998 | Duffin et al. | 607/32 |
| 5,782,878 A | 7/1998 | Morgan et al. | 607/5 |
| 5,787,155 A | 7/1998 | Luna | 379/93.09 |
| 5,835,907 A | 11/1998 | Newman | 707/10 |
| 5,836,993 A | 11/1998 | Cole | 607/59 |
| 5,838,771 A | 11/1998 | Moeller | 379/37 |
| 5,848,651 A | 12/1998 | McSheffrey et al. | 169/51 |
| 5,852,408 A | 12/1998 | Christiansen et al. | 340/870.09 |
| 5,857,966 A | 1/1999 | Clawson | 600/300 |
| 5,873,040 A | 2/1999 | Dunn et al. | 455/456.2 |
| 5,874,897 A | 2/1999 | Klempau et al. | 340/573.1 |
| 5,891,046 A | 4/1999 | Cyrus et al. | 600/510 |
| 5,891,049 A | 4/1999 | Cyrus et al. | 600/523 |
| 5,894,591 A | 4/1999 | Tamayo | 340/7.5 |
| 5,899,866 A | 5/1999 | Cyrus et al. | 600/510 |
| 5,902,234 A | 5/1999 | Webb | 600/300 |
| 5,914,675 A | 6/1999 | Tognazzini | 340/989 |
| 5,921,938 A | 7/1999 | Aoyama et al. | 600/509 |
| 5,926,133 A | 7/1999 | Green | 342/363 |
| 5,929,777 A | 7/1999 | Reynolds | 340/825.49 |
| 5,936,529 A | 8/1999 | Reisman et al. | 340/573.1 |
| 5,943,394 A | 8/1999 | Ader et al. | 379/40 |
| 5,951,485 A | 9/1999 | Cyrus et al. | 600/523 |
| 5,955,956 A | 9/1999 | Stendahl et al. | 340/635 |
| 5,970,414 A | 10/1999 | Bi et al. | 455/456.3 |
| 5,987,329 A | 11/1999 | Yost et al. | 455/456.1 |
| 5,999,493 A | 12/1999 | Olson | 368/47 |
| 6,002,936 A | 12/1999 | Roel-Ng et al. | 455/456.4 |
| 6,021,330 A | 2/2000 | Vannucci | 455/456.2 |
| 6,026,035 A | 2/2000 | Kim | 365/190 |
| 6,026,304 A | 2/2000 | Hilsenrath et al. | 455/456.2 |
| 6,028,514 A | 2/2000 | Lemelson et al. | 340/539.13 |
| 6,041,254 A | 3/2000 | Sullivan et al. | 607/5 |
| 6,041,257 A | 3/2000 | MacDuff et al. | 607/5 |
| 6,047,207 A | 4/2000 | MacDuff et al. | 600/510 |
| 6,057,758 A | 5/2000 | Dempsey et al. | 340/539.12 |
| 6,090,056 A | 7/2000 | Bystrom et al. | 601/41 |
| 6,141,584 A | 10/2000 | Rockwell et al. | 607/5 |
| 6,150,951 A | 11/2000 | Olejniczak | 340/2.8 |
| 6,201,992 B1 | 3/2001 | Freeman | 607/5 |
| 6,292,687 B1 | 9/2001 | Lowell et al. | 600/515 |
| 6,301,502 B1 | 10/2001 | Owen et al. | 607/5 |
| 6,302,844 B1 * | 10/2001 | Walker et al. | 600/300 |
| 6,304,780 B1 | 10/2001 | Owen et al. | 607/5 |
| 6,321,113 B1 | 11/2001 | Parker et al. | 607/5 |
| 6,334,070 B1 | 12/2001 | Nova et al. | 607/5 |
| 6,374,138 B1 | 4/2002 | Owen et al. | 607/5 |
| 6,405,083 B1 | 6/2002 | Rockwell et al. | 607/5 |
| 6,427,083 B1 | 7/2002 | Owen et al. | 607/5 |
| 6,438,417 B1 | 8/2002 | Rockwell et al. | 607/5 |
| 6,480,744 B1 * | 11/2002 | Ferek-Petric | 607/60 |
| 6,493,581 B1 | 12/2002 | Russell | 607/5 |
| 6,544,171 B1 | 4/2003 | Beetz et al. | 600/300 |
| 6,594,634 B1 | 7/2003 | Hampton et al. | 705/3 |
| 6,597,948 B1 | 7/2003 | Rockwell et al. | 607/5 |
| 6,624,754 B1 | 9/2003 | Hoffman et al. | 340/573.1 |
| 6,668,192 B1 | 12/2003 | Parker et al. | 607/5 |
| 6,738,671 B1 * | 5/2004 | Christophersom et al. | 607/60 |
| 2003/0025602 A1 | 2/2003 | Medema et al. | 340/568.1 |
| 2003/0058097 A1 | 3/2003 | Saltzstein et al. | 340/531 |
| 2003/0095648 A1 | 5/2003 | Kaib et al. | 379/106.02 |
| 2003/0109904 A1 | 6/2003 | Silver et al. | 607/59 |
| 2003/0120311 A1 | 6/2003 | Hansen | 607/5 |
| 2004/0124979 A1 | 7/2004 | Medema et al. | 340/539.18 |

\* cited by examiner

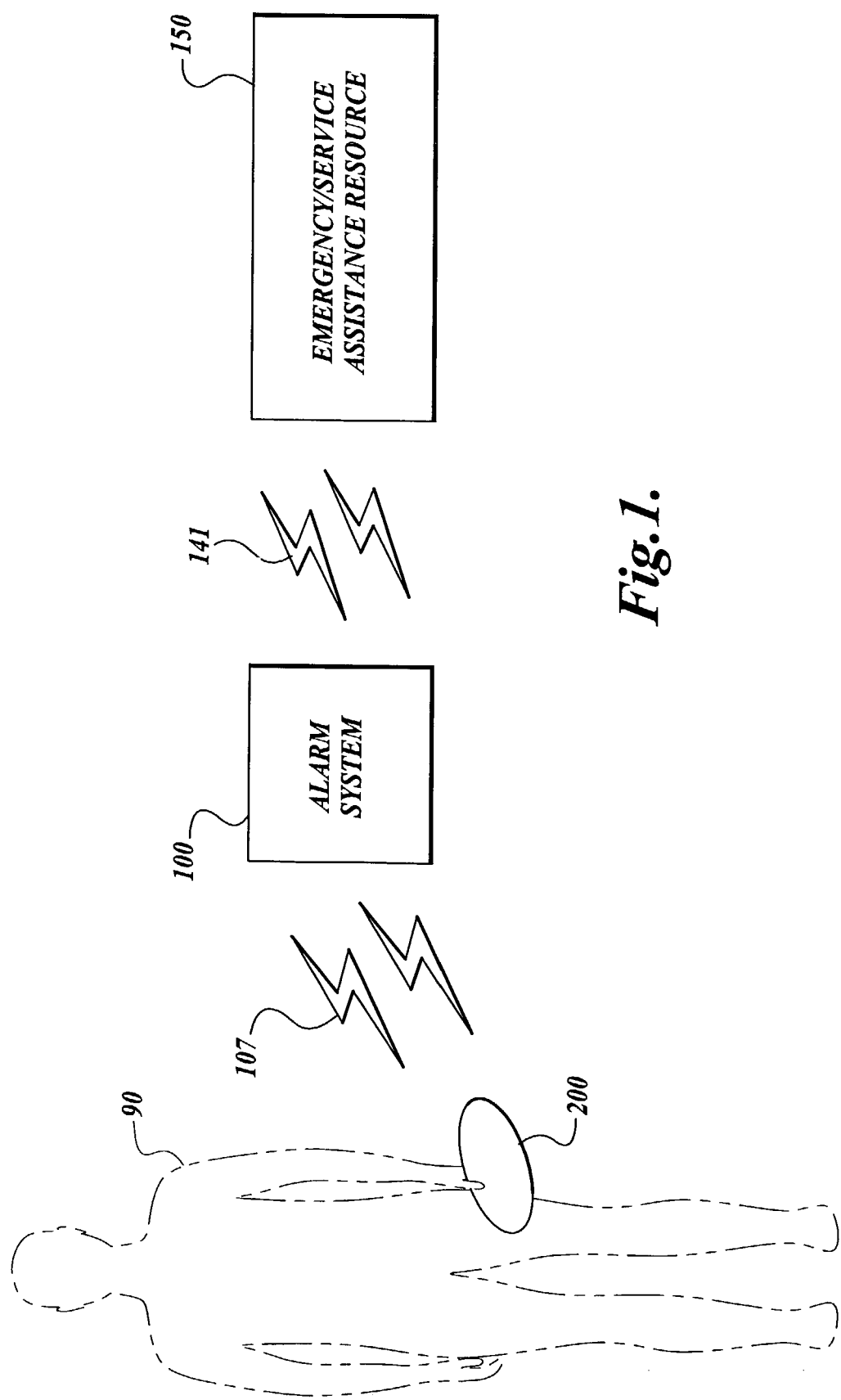

THERAPY-DELIVERING PORTABLE MEDICAL DEVICE CAPABLE OF TRIGGERING AND COMMUNICATING WITH AN ALARM SYSTEM

FIELD OF THE INVENTION

The present invention relates to portable medical devices and alarm systems, and more particularly, the present invention relates to a portable medical device that is capable of delivering therapy and triggering and/or communicating with an alarm system.

BACKGROUND OF THE INVENTION

A number of alarm systems, such as home or building alarm systems, are designed to notify emergency personnel and provide assistance in emergency situations. Most currently available alarm systems include basic monitoring capabilities to detect alarm events, such as intrusion, fire or other emergencies. Upon detection of a given event, the alarm system sends an appropriate message to a central monitoring station, typically via a land line public telephone network or a cellular link. The central monitoring station, which may be a public or private emergency service provider, typically has an attendant who can respond to the incoming alarm message by dispatching police, fire-fighters, or other third party security or emergency personnel.

Prior art alarm systems generally comprise a control station and a plurality of remote detectors. The control station houses the control circuitry and the data interfaces for communication with a central monitoring station, such as an alarm system monitoring service or an emergency 911 computer-aided dispatch system. Such circuitry may include, for example, telephone jacks, cellular transceivers and radio transponders. Some prior art systems also include interactive capabilities for providing enhanced alarm features. For example, U.S. Pat. No. 5,228,449 to Christ et al. discloses an alarm system in which the vital signs of a home care patient are monitored by a unit worn on a patient's wrist. The unit sends an alarm signal to a remote monitoring station if it detects cardiac arrest or some such other medical emergency. In addition, U.S. Pat. No. 3,843,841 to Rubenstein discloses another patient-worn monitoring device which automatically actuates a base unit to dial an emergency telephone number and deliver a prerecorded message if the patient does not reset the unit within a predetermined time after generating an alarm.

Although existing alarm systems provide sufficient capabilities for various medical needs, the capabilities of existing systems are somewhat limited in certain emergency situations, such as cardiac arrest or other conditions requiring delivery of some type of medical therapy to the patient. For example, when a victim of cardiac arrest is discovered, it is common that an alarm system require a rescuer to call for professional help. Manual steps, such as this one involving a rescuer, consume valuable time in emergency situations. In addition, emergency situations involving medical equipment, such as an automated external defibrillator (AED), sometimes require the assistance of a trained professional to respond and render aid. In a situation where a rescuer does not have sufficient training or cannot locate the proper assistance to operate any such device, the rescuer may have to call for help before rendering aid to the victim. This action can take valuable time and attention away from proper treatment to an injured person. In other scenarios, even when a rescuer calls a 911 service, the location of the victim or the distance of the communication link may make effective assistance impractical or impossible.

Thus, certain emergency situations, such as cardiac arrest or a heart failure, create a need for a system and method that provides assistance in rendering quick and effective aid. In addition, there exists a need for a system to provide more immediate medical attention without the need of a rescuer to spend valuable time requesting emergency aid or to operate complicated medical devices necessary to render aid.

SUMMARY OF THE INVENTION

The present invention provides a therapy-delivering, portable medical device capable of triggering and/or communicating with an alarm system, as well as a related system and method therefor. The portable medical device may be configured to deliver therapy to a patient, wherein the therapy delivered to the patient may be any or combination of medial therapies, e.g., defibrillation, drugs, etc., for any one or combination of medical applications, such as stroke, cardiac arrest, acute myocardial infarction (AMI), diabetic shock, etc. The portable medical device may be configured to allow an operator located at the alarm system to control or provide medical therapy to the user of the portable medical device via signals transmitted over a communication link. The portable medical device is configured to establish a communication link with an alarm system such as a residential or business alarm, upon the occurrence of a triggering event. Triggering events may be related to the use, operation or deployment of the portable medical device in an emergency situation, or they may be for service or maintenance purposes, e.g., to report device failures, system checks, etc.

One aspect of the present invention provides a method for communicating data between an alarm system and a portable medical device capable of delivering therapy. The method comprises determining the presence of a triggering event, establishing a communication link between the portable medical device capable of delivering therapy and the alarm system, and communicating the triggering event and data related thereto between the portable medical device and the alarm system via the communication link. The method further comprises initiating a response to the triggering event.

In one embodiment, the transmission of the data that describes the triggering event originates from the medical device and is sent to the alarm system. In another embodiment, the transmission of the data that describes the triggering event originates from the alarm system, and is sent to the medical device. The communication link between the medical device and the alarm system may be established when the medical device is activated or the communications link may be made in response to determining the presence of the triggering event.

In one embodiment, the system utilizes a communication link between the medical device and a central monitoring station, such as an alarm monitoring system or 911 center, to dispatch emergency resources, such as an ambulance. The communication link between the medical device and the central monitoring station may be made from a telephone or computer network and creates a two-way communication channel between the central monitoring station and the portable device.

In one embodiment, the portable medical device is conveniently sized so it can operate as an internal or external body-worn device. In an alternative embodiment, the portable medical device comprises a global positioning system (GPS) or E-911 system for determining and communicating the location of the portable medical device.

In yet another embodiment, the portable medical device is in the form of a stand-alone unit that is configured to communicate status information of the portable medical device to the alarm system. In one example, the portable medical device communicates an alarm signal to the alarm system when the portable medical device is deployed or removed from a docking station. In another example, the portable medical device is configured to communicate other status information such as a battery failure, mechanical failure, or other function failure of the device.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 is a schematic block diagram of a therapy-delivering, portable medical device triggering and/or communicating with an alarm system in accordance with the present invention;

DETAILED DESCRIPTION OF THE PRESENT INVENTION

Figure 2A:
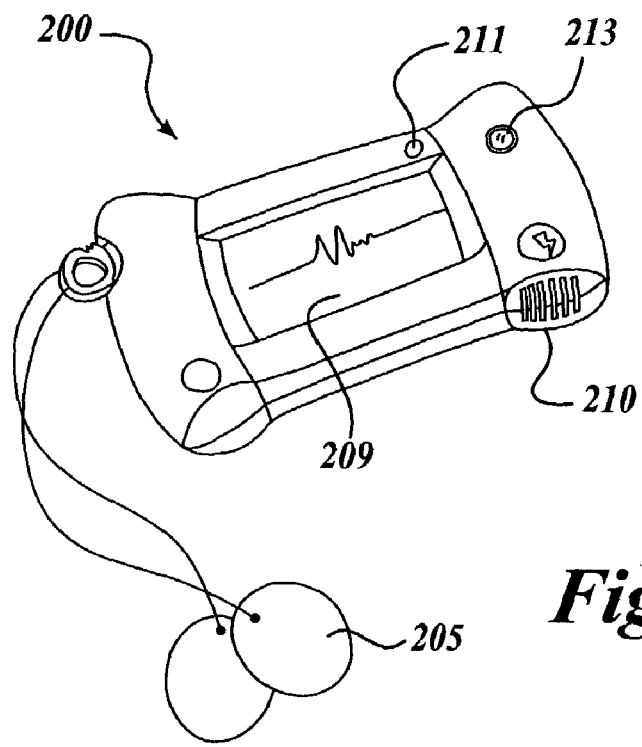
FIGS. 2A–2B are perspective pictorial views of two exemplary embodiments of a therapy-delivering, portable medical device capable of triggering and communicating with the alarm system shown in FIG. 1.

The present invention provides a therapy-delivering, portable medical device for triggering and communicating with an alarm system, such as an existing residential or business alarm system, and a related method and system therefor. FIG. 1 is a schematic block diagram of such a device and alarm system. As will be described in more detail below, upon the occurrence of a trigger event, a portable medical device 200 capable of delivering therapy establishes a communication link 107 (if one has not been established already) with an alarm system 100, such as a residential or business alarm system. Once the communication link 107 has been established, the portable medical device 200 sends a notification of the trigger event to the alarm system 100. If the trigger event occurs in an emergency context, the alarm system 100 may alert an emergency assistance resource 150 via a communication link 141 and request emergency assistance. It will be appreciated that an emergency assistance resource 150 can be any emergency assistance service. For example, the emergency assistance resource 150 may comprise any public or private emergency assistance service such as an ambulance, firefighter or police service, or any other third-party security service. In addition to, or perhaps in lieu of, alerting the emergency assistance resource 150, the alarm system 100 may provide information and/or instructions to the portable medical device 200 relating to the operation of the device, treatment of the patient, delivery of therapy, status of the emergency assistance, etc.

In the emergency context, a trigger event is an event frequently associated with the treatment of a patient experiencing a medical emergency. Accordingly, a trigger event may occur as soon as the medical device is deployed from a docking station or wall mount in which it resides when not in use. In such an embodiment, the docking station and/or medical device 200 includes the necessary components for detecting the removal of the device. Such components may include mechanical, electrical, optical, magnetic, etc. switches or sensors, or some combination thereof for detecting removal of the portable medical device. An emergency trigger event can also occur upon activation (turning on) of the portable medical device at an unscheduled or unexpected time (it will be appreciated that the device may self-activate at predetermined times for scheduled maintenance). An emergency trigger event may also occur at any point deemed desirable following activation, e.g., upon attachment of electrodes to the patient in the case of an AED, upon expiration of some predetermined time interval following activation, upon user instruction via the user interface of the medical device, upon detection of a medical condition, requiring delivery of therapy, etc. An emergency trigger event may also occur upon the detection of a predetermined health condition. For example, an emergency trigger event may occur if a monitored patient parameter falls below or exceeds a certain threshold, e.g., a rise in temperature or blood pressure, rise or fall in heart rate, fallen oxygen saturation or increase in expired carbon dioxide. An emergency trigger event may also occur for reasons other than patient treatment, device deployment or device use. For example, an emergency trigger event may occur if the portable medical device is stolen (which may be detected by constantly monitoring a local parameter, such as an ambient temperature, and determining that the device has been removed from its assigned location if a parameter falls outside a predetermined range). Finally, the emergency trigger event may occur as a result of a user-initiated action, such as depressing a "call 911" button with which the medical device or its docking station is equipped. Accordingly, any events that require emergency or security assistance may be considered emergency trigger events.

In yet other embodiments of the present invention, the trigger event does not occur in an emergency context. Rather, the trigger event occurs in a service context. More specifically, the trigger event is an event relating to the service, status or maintenance of the portable medical device 200. Such service trigger events may occur according to a certain time schedule stored in memory of the device. For example, a component of the medical device has expired or is about to expire (e.g., usable life of batteries or electrodes has or is about to expire); the designated user of the device needs to be retrained (e.g., typically, a nontraditional AED user needs to be retrained at least once a year); the device requires routine maintenance; the medical device or a component thereof is malfunctioning or requires maintenance as determined by a periodically conducted self-test (e.g., the voltage level of a power source is too low). In yet other embodiments of the present invention, the service trigger event may be a periodic request from the device to receive software upgrade information. The service trigger event may also occur at an unscheduled or unexpected time, for example, upon unexpected deactivation or malfunction of the device. Further, the service trigger event may occur as the result of a user-initiated action, such as depressing a service or training request button with which the medical device or its docking station is equipped. It will be appreciated that any events that require servicing or maintenance may be considered service trigger events.

Accordingly, the device 200 may send a notification of the service trigger event to the alarm system 100 via the communication link 107. In turn, the alarm system may alert a service assistance resource 150 of the service trigger event via communication link 141 and request service assistance. It will be appreciated that the service assistance resource can be any resource for providing public or private service assistance such as field technicians, manufacturer customer support, etc. In addition to, or perhaps in lieu of, alerting a service resource, the alarm system 100, if capable, may provide the device with the required service or simply record the service trigger event and/or results of any self-tests, status reports, service requests, etc. for reporting purposes. For example, if the service trigger event is a request for a software upgrade and the alarm system 100 stores the requested upgrade, the alarm system 100 may download the requested upgrade to the device for installation.

Finally, in yet other embodiments of the present invention, the trigger event is initiated by the alarm system 100 rather than the device 200. For example, in the service context, the alarm system 100 may send the device 200 instructions to perform certain system and maintenance testing or may download a software upgrade to the device 200 via the communication link 107. In an emergency context, the alarm system 100 may be independently notified of a trigger event, e.g., via a 911 call, and may instruct the portable medical device to activate and perhaps issue an audible and/or visual tone to indicate its location.

As will be described in more detail below, the therapy-delivering, portable medical device 200 includes the necessary circuitry for establishing the communication link 107 with the alarm system 100. It will be appreciated that the communication link 107 (and communication link 141, for that matter) may be established utilizing any one or combination of a variety of communications media and/or communication protocols or methods to transfer data in any form, e.g., video, audio, digital, etc. Examples of suitable wired communications media/methods include, but are not limited to, public switched telephone networks ("PSTN"), wired digital data networks, such as the Internet or a local area network ("LAN"), co-axial cable, fiber optic cable and the like. Examples of suitable wireless communications media/methods include, but are not limited to, wireless telephony ("cellular") including analog cellular, digital personal communications service ("PCS"), short message service ("SMS"), and wireless application protocol ("WAP"). Other suitable wireless communication media/methods include, but are not limited to, wireless digital data networks, such as 802.11 wireless LAN ("WLAN"), two-way paging networks, specialized mobile radio systems, infrared, and non-licensed ISM-service communications links, such as Bluetooth. Further, some communication methods, either wired or wireless, include Internet protocol ("IP") addressing. One skilled in the relevant art will appreciate that additional or alternative communication media/methods may be practiced and are considered within the scope of the present invention.

In accordance with the present invention, the medical device 200 that triggers and communicates with the alarm system 100 is a portable medical device configured to deliver therapy to a patient. For example, the portable medical device 200 may deliver any one or combination of medical therapies, e.g., defibrillation shock or other electrical stimuli, drugs, thermal coolants, CPR (or other care) instructions, etc., for any one or combination of medical applications such as cardiac arrest, AMI, stroke, diabetic shock, etc. Accordingly, for brevity, such a therapy-delivering, portable medical device is referred to herein simply as a "portable medical device" or "medical device."

FIG. 2A is a pictorial representation of one embodiment of a therapy-delivering, portable medical device 200 capable of triggering and communicating with the alarm system 100. In the embodiment shown in FIG. 2A, the portable medical device is an automated external defibrillator (AED) capable of delivering a defibrillation shock to a patient experiencing ventricular fibrillation. Although an AED is shown in FIG. 2A, it will be appreciated that, in accordance with the present invention, any portable medical device (including implantable devices) may be equipped with the necessary hardware and software for triggering and communicating with the alarm system 100. As shown in FIG. 2A, the portable medical device 200 is constructed from a high strength plastic or metal, where the casing of the portable medical device 200 is formed in a relatively small housing having at least two sides. A user display 209 is oriented on one side of the portable medical device 200 and positioned such that an operator of the device can easily view the displayed data. In one embodiment, the user display 209 is configured from a liquid crystal display (LCD) capable of producing text and graphics displays. The user display 209 is also capable of receiving data entry from an operator. As known to one skilled in the art, an LCD screen can be configured with a touch sensitive film for receiving key entries, wherein the keys of the touch screen are displayed on the LCD.

Figure 3:
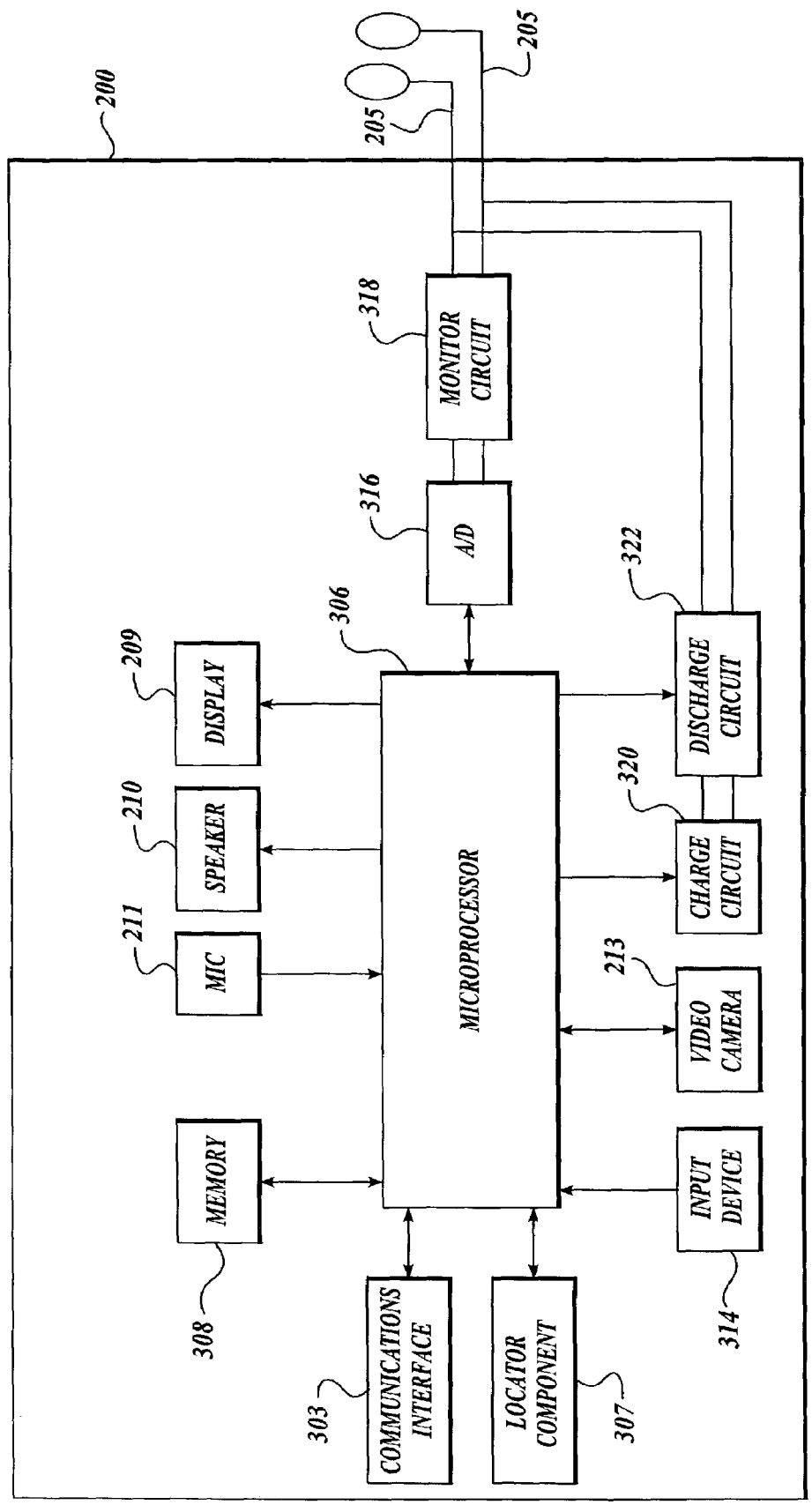
FIG. 3 is a schematic block diagram of the components of the portable medical devices depicted in FIGS. 2A and 2B.

The portable medical device 200 also includes a microphone 211, a speaker 210, and a video camera 213. As described below with reference to FIG. 3, these audio and video interface devices are interconnected through the internal circuitry of the portable medical device 200 and are capable of allowing audio and visual communication between an operator of the device and the alarm system 100. The microphone 211 and speaker 210 are electronically connected to an audio interface 212 in a configuration similar to that of an audio configuration of a personal computer.

As also illustrated in FIG. 2A, the portable medical device 200 includes at least two electrodes 205. As will be described in more detail below, the electrodes 205 are electronically connected to the internal circuitry of the portable medical device 200. As known to one skilled in the art, the electrodes 205 are configured to receive electrocardiogram (ECG) signals from the patient and deliver a defibrillation shock to the patient if a shockable heart rhythm is detected by the AED.

Figure 2B:
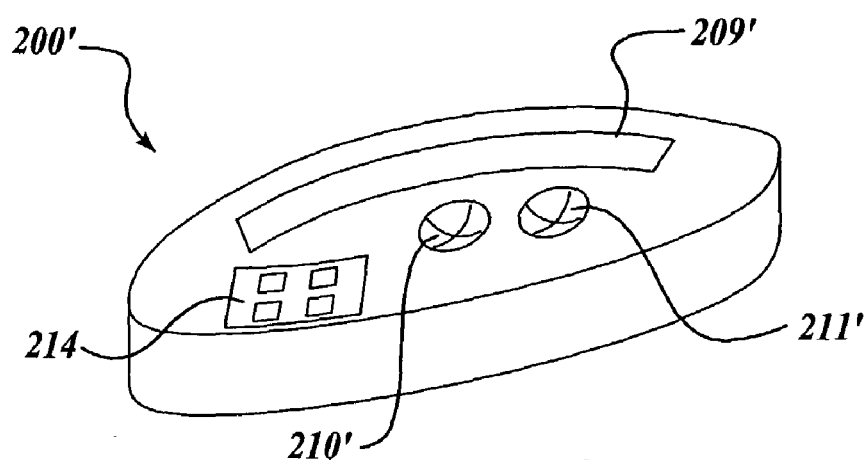

FIG. 2B is a perspective view of yet another embodiment of a portable medical device 200' that is sized for a patient to wear or carry while in normal operation. As shown in FIG. 2B, one embodiment of the portable medical device 200' comprises a control panel 214, a speaker 210', a microphone 211', and a user display 209'.

Now that the overall design of an AED capable of triggering an alarm system has been discussed, several key AED components will be discussed in more detail. However, since the internal components of both embodiments of the portable medical device 200' and 201' are essentially the same, the description of these components will be made with reference to device 200 as depicted in FIG. 2A. As shown in more detail in FIG. 3, the portable medical device 200 includes a microprocessor 306 that controls the operation of the device 200. The microprocessor 306 is connected to the user display 204, the speaker 210, the microphone 211, and the input device 314. In portable medical device 200, the microprocessor 306 is also connected to a video camera 213 used to record video images of the operator and/or patient. The microprocessor 306 is also connected to a memory 308 which stores program code necessary for operation of the device. In yet other embodiments of the present invention, the memory stores a voice recognition software module which allows the rescuer or patient to operate the device 200 and respond to visual and/or aural instructions via voice command rather than using the input device 14. Such a module in combination with a microphone would then provide the rescuer or patient with hands-free operation of the device 200. The device 200 also includes a communications interface 303 for establishing a communication link 107 with the alarm system 100.

During defibrillation operation, the microprocessor 306 analyzes an electrocardiogram (ECG) of a patient using an automatic heart rhythm detection algorithm also stored in memory 308 to identify whether the patient is experiencing a shockable heart rhythm, such as ventricular fibrillation. The detection algorithm executed by the microprocessor 306 in one embodiment of the present invention described herein is similar to that used in the LIFEPAK® 500 defibrillator provided by Medtronic Physio-Control Corp. of Redmond, Wash., the assignee of the present invention. Other known heart rhythm detection algorithms may also be used without departing from the scope of the present invention, such as those algorithms designed to comply with standards promulgated by the Association for the Advancement of Medical Instruments (AAMI).

The ECG signals analyzed by the detection algorithm are collected by the electrodes 205 and passed through a monitor circuit 318 to an analog-to-digital converter 316. The analog-to-digital converter 316 then passes the digitized signals to microprocessor 306. If the microprocessor 306 detects a shockable rhythm, the microprocessor causes a charging circuit 320 to generate a current causing a storage capacitor (not shown) to charge in preparation for delivery of a defibrillation shock. When the capacitor is fully charged, and delivery of the defibrillation pulse initiated, a discharge circuit 322 coupled to the microprocessor 306 and charge circuit 320 discharges the defibrillation shock to the electrodes 205 for application of the defibrillation shock to the patient 90. In one embodiment of the present invention, the discharge circuit 320 is an H-Bridge circuit of the type described in commonly-owned U.S. Pat. No. 6,041,254, entitled "H-Bridge Circuit for Generating a High-Energy Biphasic Waveform in an External Defibrillator and further including a Protective Component that Has both Inductive and Resistive Properties," which patent is specifically incorporated herein by reference.

As noted above and shown in FIG. 3, the portable medical device 200 also includes a communications interface 303 for providing a communications link 107 with the alarm system 100. The communications interface 303 may be configured to provide an aural, visual and/or data communication link between the portable medical device 200 and the alarm system 100. Accordingly, those of ordinary skill in the art will appreciate that the communications interface 303 is constructed with commercially available circuitry appropriate for the particular type of communication link 107. For example, if the communication link 107 is established via a wireless telephony network, communications interface 303 is constructed from components analogous to the electronics used for wireless digital communications with such a network.

In yet other embodiments of the present invention, the communication interface may not be resident in the medical device 200. Rather, the communications interface 303 is resident in the docking station, wall mount or other enclosure in which the medical device is housed.

Although a one-way communication link between the portable medical device 200 and the alarm system 100 is possible, in the embodiment shown in FIG. 1, the portable medical device 200 establishes a two-way or bi-directional communication link 107 with the alarm system 100. The bi-directional communication link allows the alarm system 100 to transmit and receive patient, medical, location and/or device information to and from the portable medical device 200. It will be appreciated that any type of information or data may be communicated between the portable medical device 200 and the alarm system 100, whether patient-related, medical-related, location-related, or device-related. For example, such information may include, but is not limited to, patient identification data, ECG data, self-test data, program code, maintenance data, service data, diagnostic data, treatment data, operator instructions, emergency instructions, etc.

In addition to patient, medical and device information, the portable medical device 200 may also provide location information to the alarm system 100. Accordingly, the portable medical device 200 includes a locator component 307 connected to the microprocessor 306 for determining the location of the portable medical device 200 (see FIG. 3). The location information is then sent to the alarm system 100 by the communications interface 303 via the communications link 107. In one embodiment, the locator component 307 comprises a global positioning system (GPS) receiver. Since portable GPS circuitry is well known to those skilled in the art, the GPS receiver 307 will not be described in further detail herein.

In yet another embodiment, the portable medical device 200 may include a locator component 307 comprising an automatic location identification ("ALI") enabled data communicator for determining the location of the device 200. In the present description, the term ALI (automatic location identification) is used to refer to the location identification capability in compliance with the Enhanced 911 standard prescribed by the United States Federal Communications Commission (hereinafter "the E911 standard"). Specifically, pursuant to the E911 standard, cellular phone service providers within the United States must provide by Oct. 1, 2001 the capability to locate the position of a cellular phone making an emergency (911) call within the provider's system, and this capability is called ALI. ALI may be accomplished using handset-based technologies or solutions, e.g., a cellular phone equipped to self-identify its location, which may incorporate a GPS receiver. In one embodiment, the ALI-enabled communicator is adapted to identify the location of the portable medical device 200. Alternatively, ALI may be accomplished using network-based technologies or solutions, wherein the location of a portable medical device 200 is identified based on a communication link connecting the ALI-enabled communicator and a remote locating service located in the alarm system 100. For example, certain cellular phone systems track the strength, the angle, and the arrival time difference of transmission signals for determining a cell phone's location, using time difference of arrival (TDOA) technology or timing advance (TA) location measurement technology. In this embodiment, the location of the portable medical device 200 is identified by the alarm system 100, and the identified location may or may not be relayed to the ALI-enabled communicator of the device 200. Further alternatively, ALI may be based on a combination of both handset-based technologies and network-based technologies. For handset-based solutions, the E911 standard requires that a call locations be identified within 50 meters for 67% of calls, and 150 meters for 95% of calls. For network-based solutions, a call location must be identified within 100 meters for 67% of calls, and within 300 meters for 95% of calls. A variety of ALI techniques are under development and/or available, some of which can be found in U.S. Pat. Nos. 5,926,133; 5,970,414; 5,987,329; 6,002,936; 6,021,330; 6,026,035; and 6,026,304, all incorporated herein by reference. Accordingly, the term "wireless ALI-capable system," as used in the present description, refers to any wireless system that meets the E911 standard regardless of particular technologies used to meet the standard.

It should be appreciated that those skilled in the art can readily apply any ALI technologies developed to meet the E911 standard in countries other than the United States, where emergency medical service phone numbers are other than 911. In other words, a wireless ALI-capable system of the present invention is equally implementable in countries other than the United States without undue experimentation, and therefore is intended to encompass all such ALI-capable systems applied in various networks in various countries.

It should further be appreciated by those skilled in the art that, although the E911 standard relates to only 911 emergency calls placed to an emergency response central dispatch, any ALI-capable system can be equally applied to determine the location of an ALI-enabled communicator, such as a cellular phone, placing a call to any number. Therefore, the term "wireless ALI-capable system" as used in the present invention encompasses all such systems, wherein the remote location service is not necessarily situated at an emergency response central dispatch and associated with an emergency call number. For example, the remote locating service may be operated by a person, perhaps a residential or business alarm station attendant or computer system, in charge of centrally monitoring and maintaining one or more medical devices, as more fully described below.

Figure 4:
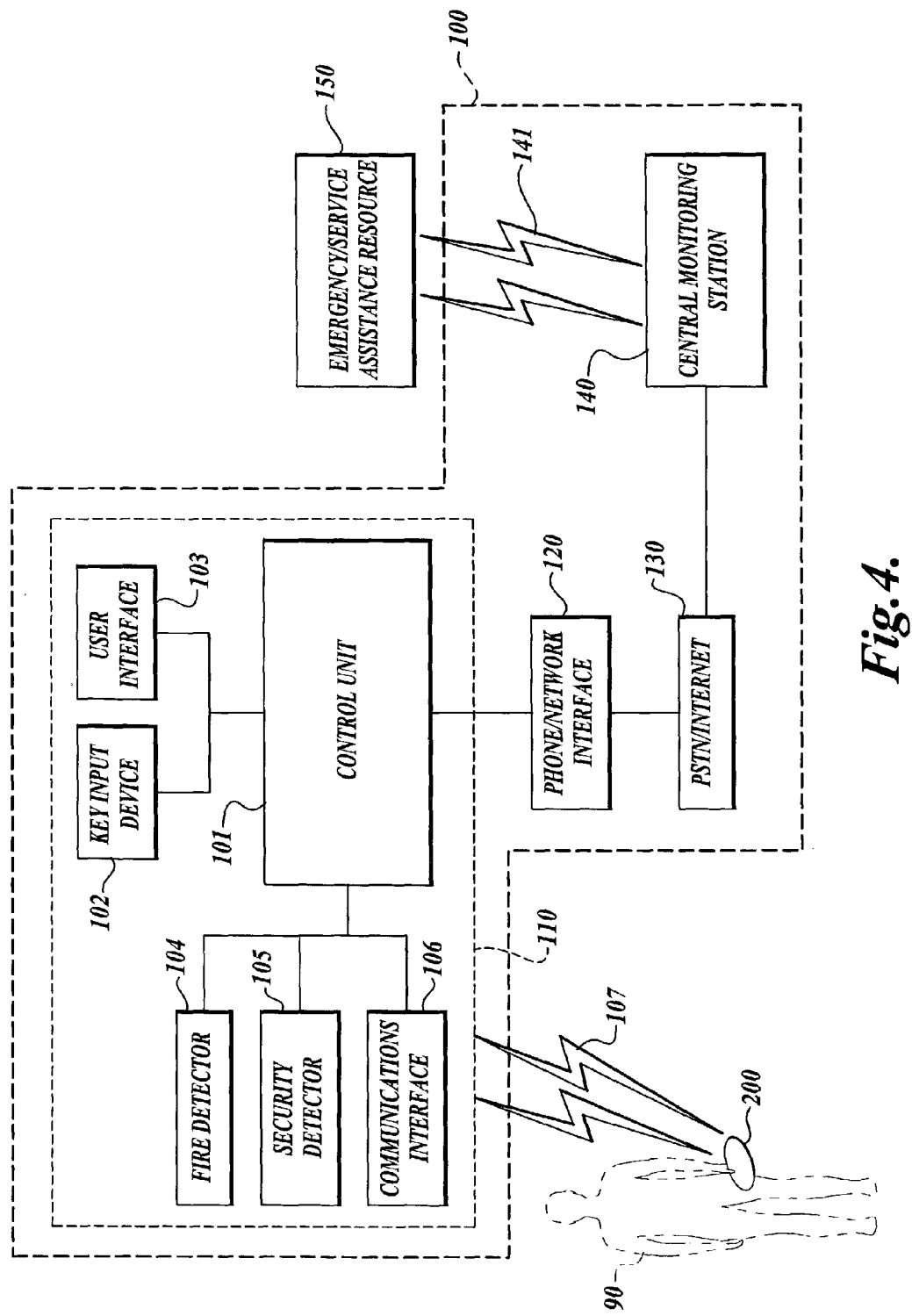
FIG. 4 is a block diagram of an alarm system comprising a central control station and a remote, central monitoring station in direct communication with a portable medical device.

Now that one type of portable medical device 200 capable of delivering therapy has been described in detail (i.e., an AED), several more detailed embodiments of the alarm systems capable of being triggered by a portable medical device shall be discussed. For example, FIG. 4 is a schematic block diagram of an alarm system 100 comprising a central control station 110 connected via a publicly switched telephone network (PSTN) 130 (or other network connection, e.g., Internet), and a telephone/network interface 120 to a central monitoring station 140. The telephone/network interface 120 may comprise a network TCP/IP circuit or a telephone modem. As known to one skilled in the art, the telephone/network interface 120 may comprise any circuit capable of providing data communication between a local computing device and a remote computing device. Although computer-type architecture is used in this embodiment, the scope of the present invention also includes other electronic interfaces that are designed to communicate through any wired or wireless communication system.

When a trigger event occurs in an emergency context, the central control station 110 notifies the central monitoring station 140 via the telephone/network interface 120 and PSTN 130. In turn, the central monitoring station 140 may alert an emergency assistance resource 150, e.g., fire, police, ambulance, etc., and request emergency assistance. The central monitoring station 140 and the emergency assistance resource 150 may communicate with a wireless or wired communication link 141, as noted above.

Similarly, if the medical device initiates trigger event in the service context, the central control station 100 notifies the central monitoring station 140, which in turn, may alert a service assistance resource 150, e.g., field technicians, manufacturer/customer support, etc., and request service assistance.

Conversely, the service or emergency trigger event may be initiated by the alarm system 100. Accordingly, either the central control station 110 or the central monitoring station 140 initiates the emergency or service trigger event and the trigger event is then passed on to the portable medical device 200 via the communication link 107.

The central monitoring station 140 may comprise a third-party alarm monitoring service having operator services that communicate to an emergency/service assistance resource 150. Alternatively, the central monitoring station 140 may comprise a computerized system (e.g., an emergency 911 computer-aided dispatch service) for receiving alarm signals from a number of alarm units, such as the central control station 110, where the central monitoring station 140 is configured to automatically relay alarm information to a emergency/service assistance resource 150. The central monitoring station 140 may be manned by a human operator or may be a completely automated, computerized system.

In order to provide the trigger event notification discussed above, the central control station 110 houses the necessary communications circuitry for providing communication between the central monitoring station 140 and the portable medical device 200. In addition, the central control station 110 is constructed from components used in known residential or business alarm systems. For example, existing residential or business alarm systems may include a number of components for detecting motion, fire, breach of security and/or a combination thereof. In one embodiment, a fire detector 104 is located in a region of a building or residence to create a protected region for detecting fire or smoke. In addition, a security detector 105 is placed near entryways for intruder detection. The security detector 105 may comprise an infrared sensor for detecting motion or the security detector 105 may comprise one or more electromechanical devices for detecting the opening or closing of an entryway.

The central control station 110 also comprises a control unit 101, a key input device 102, and a user interface 103. The control unit 101 comprises a programmed computer processor (not shown) to control and monitor the key input device 102, user interface 103, fire detector 104, the security detector 105, and a communications interface 106. In addition, the control unit 101 may be configured to communicate with remote devices or systems (such as the central monitoring station 140) via the PSTN 130 and telephone/network interface 120. Similar to a personal computer, the key input device 102 and user interface 103 are configured for communication and control capabilities for an attendant of the central control station 110. In one embodiment, the user interface 103 may comprise a video monitor having key entry capabilities. As known to one skilled in the art, each component of the central control station 110 may communicate through circuitry that is of similar construction to a personal computer, e.g., by the use of a data bus, serial link or other like forms of electronic communication.

As also shown in FIG. 4, the central control station 110 comprises a communications interface 106 coupled to the control unit 101 capable of communicating with the communications interface 303 of portable medical device 200 via the communication link 107. Accordingly, those of ordinary skill in the art will appreciate that the communications interface 106 is constructed with commercially available circuitry appropriate for the particular type of communication link 107. For example, if the communication link 107 is established via a wireless telephony network, communication interface 106 is constructed from components analogous to the electronics used for wireless digital communications with such a network. In another embodiment, the communications interface 106 may comprise a radio communication circuit configured to provide a two-way radio communication link between the central control station 110 and the portable medical device 200. In such an embodiment, the radio communication circuit is constructed from commercially available electronic components that transmit and receive digital or analog signals and that are capable of video, audio and data communication.

As noted above, the two-way data communication link 107 may be established between the portable medical device 200 and the central control station 110 and may support audio, video and/or data (such as a rescuer or patient) communication therebetween. Alternatively, by the use of the PSTN 130, audio, video, and/or data signals can be communicated between the portable medical device 200 and the central monitoring station 140 or emergency service assistance resource 150. By virtue of this two-way audio/video/data communication link 107 and the user interface components of the medical device 200 (e.g., the user display 209, microphone 211, speaker 210, video camera 213 described above), a person or computer system at a remote location can assist the user of the portable medical device 200 operate the device, service the device, treat the patient, deliver therapy, etc. in real-time. More specifically, instructions for delivering therapy, operating the device, treating the patient, performing service functions, etc., may be sent from the central control station 110, the central monitoring station 140 or the emergency/service assistance resource 150 (or from a user located at the central control station 110, central monitoring station 140 or emergency/service assistance resource 150) to the portable medical device 200 in the form of voice instructions, text messages, video images, graphical illustrations, etc. In addition, instructions generated by pre-programmed, protocol driven instruction sets may be sent or prompted for display by the medical device.

Figure 5:
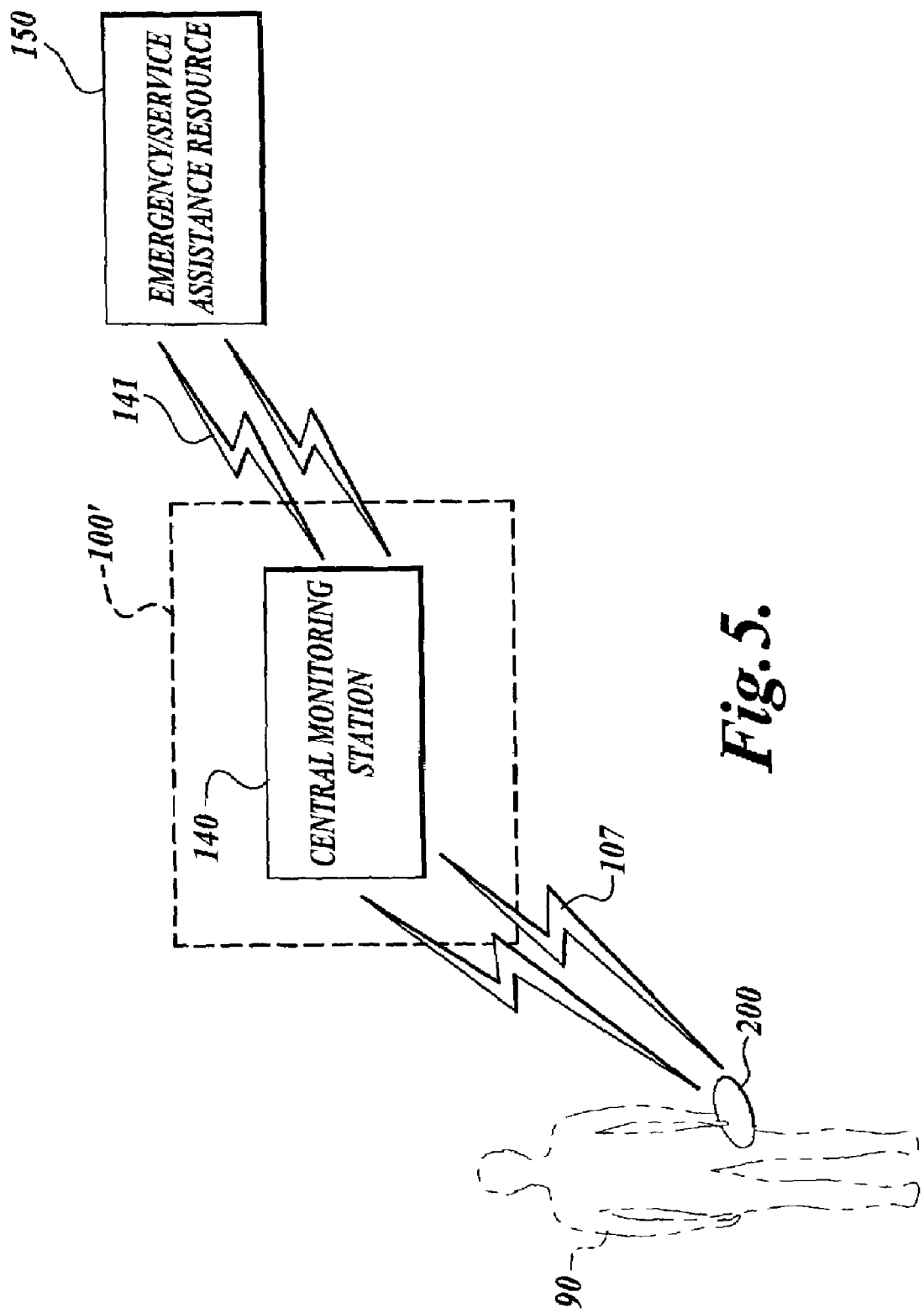
FIG. 5 is a block diagram of an alarm system comprising a remote, central monitoring station in direct communication with a portable medical device.

Referring to FIG. 5, another embodiment of an alarm system 100' capable of being triggered and communicating with a portable medical device 200 is shown. The embodiment depicted in FIG. 5 is similar to the embodiment depicted in FIG. 4, however, the portable medical device 200 is configured to establish a communication link 107 directly with a central monitoring station 140. As noted above, the communication link 107 may be established utilizing any one or combination of a variety of communications media and/or communications protocols or methods to transfer data. Accordingly, it will be appreciated that the central monitoring station 140 includes a communications interface similar to the communications interface 106 of the central control station 110 described above. For example, the communication interface of the central monitoring station 140 may be constructed with communication electronics of a pager or wireless telephone configured to communicate information via a serial port to the portable medical device 200. In yet other embodiments, the communications interface may be a radio communication circuit, telephone modem or network interface.

Figure 6:
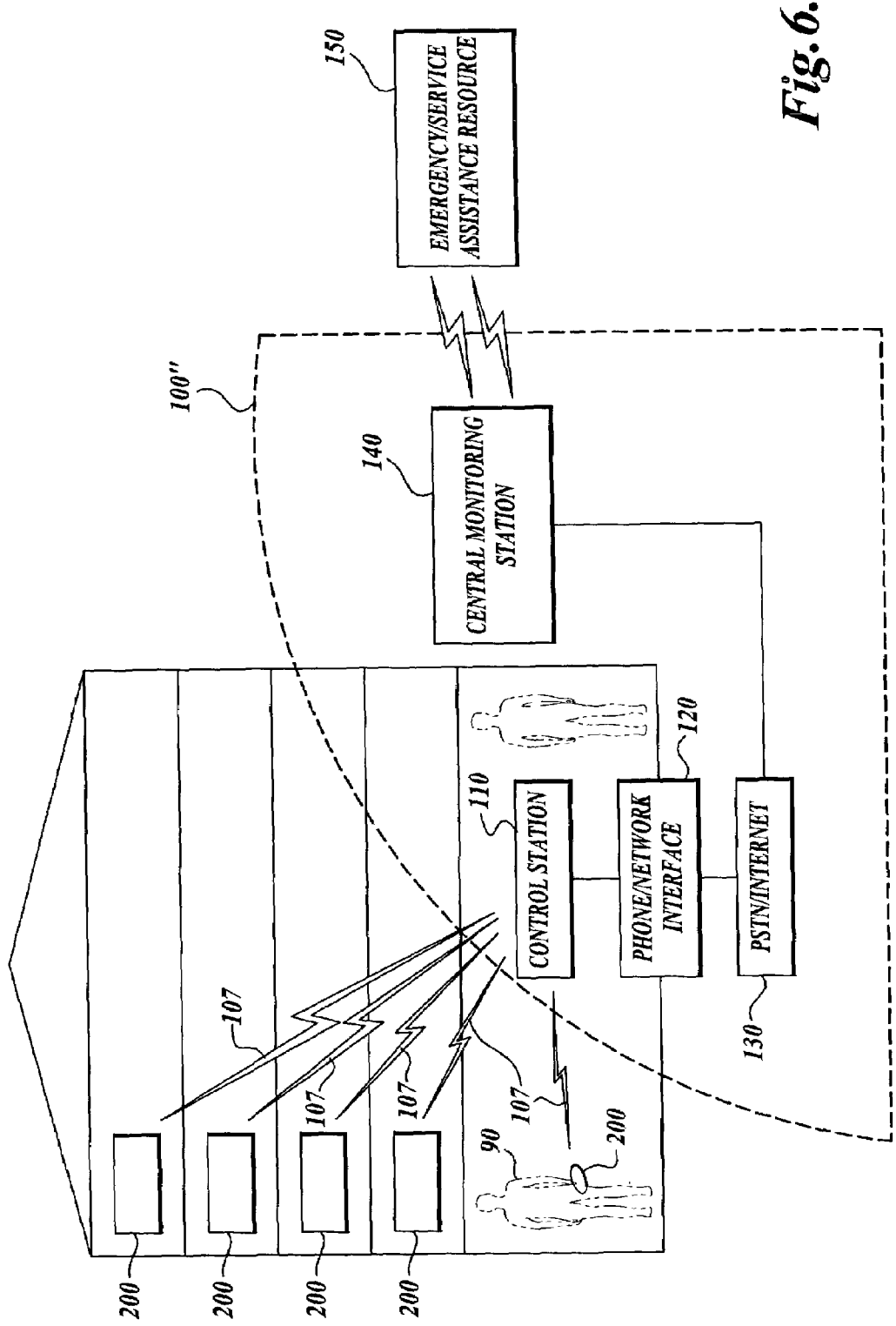
FIG. 6 is a block diagram of an alarm system capable of being triggered by and/or communicating with a plurality of portable medical devices.

Referring to FIG. 6, another embodiment of an alarm system 100" capable of communicating with and being triggered by a plurality of portable medical devices 200 is shown. In the embodiment illustrated in FIG. 6, the alarm system 100" comprises a central control station 110 connected to a central monitoring station 140 via PSTN 130 or other network connection, e.g., the Internet, and a telephone/network interface 120. Such an alarm system could be found in an apartment building, office building, shopping mall, etc., i.e., anywhere multiple portable medical devices may be deemed useful. The alarm system 100" is very similar to that described above with reference to FIG. 4. However, the embodiment of FIG. 6 comprises a plurality of similar or dissimilar portable medical devices 200, each capable of triggering the alarm system 100" and transmitting and/or receiving patient, medical, location and/or device data to and from the central control station 110 via similar or dissimilar communication links 107. As also described above in connection with FIG. 3, in one embodiment each portable medical device 200 includes a communications interface 303 that accommodates wireless or wired data communications with the central control station 110 via a communication link 107. Each communications link 107 may comprise any one or a combination of the various communications media/methods also described above. Accordingly, when any of the portable medical devices 200 capable of communicating with the central control station 110 is deployed or activated, the alarm system 100" may be triggered and assistance resources provided.

Figure 7:
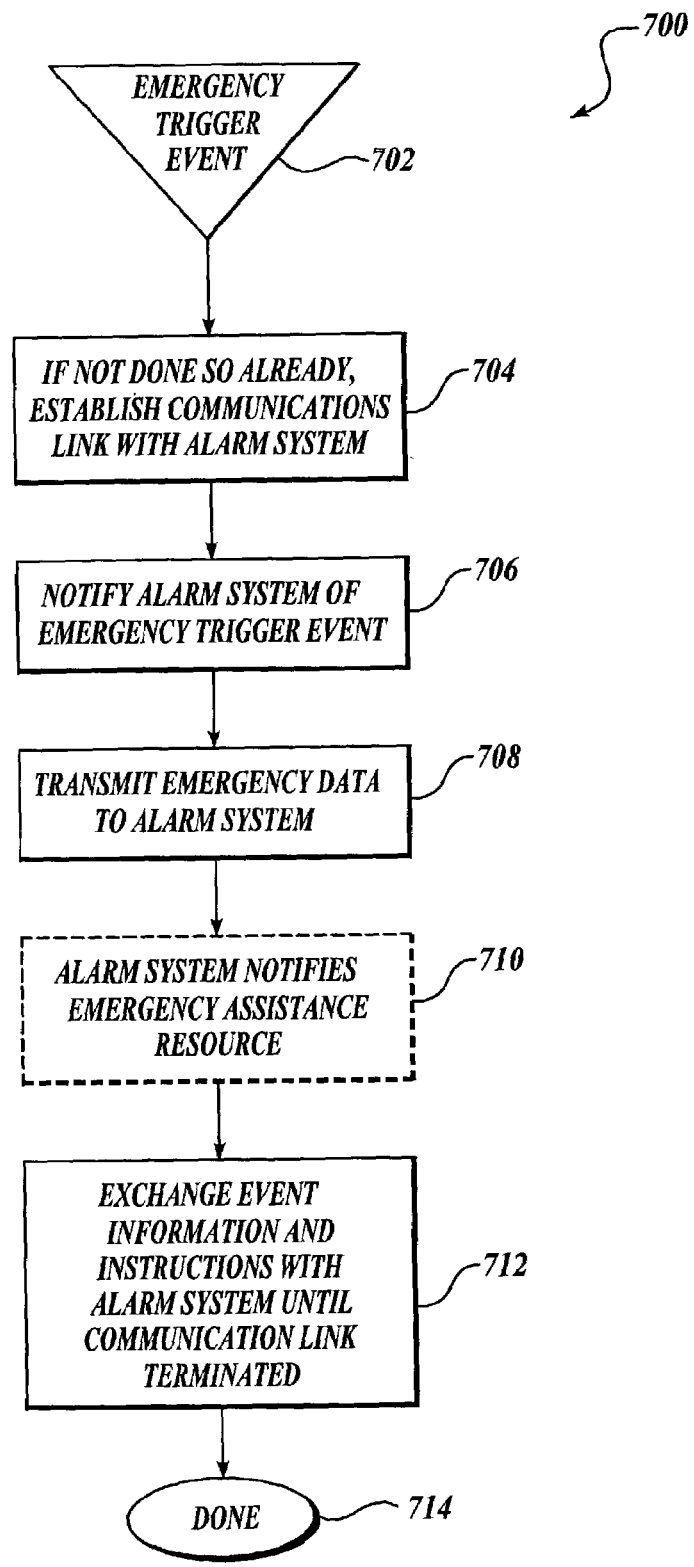
FIG. 7 is a flow diagram of a method by which a therapy-delivering, portable medical device triggers and communicates with an alarm system upon the occurrence of an emergency event.

Now that various alarm system embodiments have been described, the methods used by a portable medical device 200 to trigger and/or communicate with an alarm system 100 will be discussed. FIG. 7 depicts a flow diagram of a method 700 by which a portable medical device 200 triggers and communicates with an alarm system 100 upon the occurrence of an emergency trigger event. The method 700 begins in FIG. 7 at block 702 where an emergency trigger event occurs. As noted above, the emergency trigger event can be any one of a variety of events associated with a medical or other type of emergency. For purposes of the present example, it will be assumed that a patient is experiencing a medical emergency, and accordingly, the emergency trigger event is activation of the medical device 200.

In response to the emergency trigger event, e.g., activation of the medical device 200, the method 700 continues to block 704 where the portable medical device establishes a communication link 107 with the alarm system 100. As described above, the device may be configured to establish a bi-directional communication link with the alarm system sufficient for supporting transfer of any type of data, e.g., audio, video, etc. This allows the device and alarm system to communicate any patient, medical, location or device data to each other. In addition, this allows the alarm system to communicate to the device a confirmation of emergency response.

It will be appreciated that in some embodiments of the present invention, it is possible that the communication link between the medical device 200 and the alarm system 100 may have already been established. For example, the medical device may be in constant communication with and/or continuously monitored by the alarm system 100 (much like a node in a complete network). Accordingly, separate establishment of the communication link may be unnecessary.

Next, the method 700 continues to block 706 with a portable medical device 200 notifies the alarm system 100 of the emergency trigger event via the communication link 107. It will be appreciated that the portable medical device will format and transmit the notification of the emergency trigger event in any form or format suitable for the alarm system. Once the alarm system has been notified of the trigger event, the portable medical device 200 may begin transmitting in block 708 any additional information or data regarding the trigger event, whether patient-related, medical-related, location-related or device-related. As noted above, such information may include, but is not limited to, patient identification data, ECG data, diagnostic data, treatment data, location data, etc. As shown in block 710 (which is shown in phantom since this action is taken by the alarm system 100), upon receipt of the emergency trigger event notification from the medical device, the alarm system 100 may notify emergency resource assistance 150. Accordingly, the emergency resource assistance may dispatch emergency personnel, e.g., ambulance, fire, police, security, etc. in response to the emergency trigger event. It will be appreciated that in lieu of notifying emergency resources, it may be possible for the alarm system 100 itself to provide information and/or instructions to the portable medical device 200 relating to the operation of the device, treatment of the patient, delivery of therapy, etc.

Regardless of whether the alarm system further notifies an emergency assistance resource of the trigger event, the alarm system 100 and portable medical device 200 may exchange emergency data with one another until the communication link 107 is terminated in block 712. More specifically, once a communications link 107 has been established with alarm system 100 and the alarm system 100 has been notified of an emergency trigger event, the portable medical device 200 may continue transmitting data to the alarm system 100, and the alarm system may continue to respond. For example, if the medical device 200 is equipped with a video camera (as described above in connection with FIG. 3), the portable medical device 200 can transmit video images captured by the video camera to the alarm system 100. The alarm system 100 can record such data for reporting purposes and/or post-processing. In addition, the alarm system 100 (or system attendant, security guard, etc.) can evaluate the data and send further information and/or instructions back to the medical device 200. For example, in one embodiment of the present invention, the alarm system 100 (or user thereof) can send visual (e.g., video, graphical, textual, etc.) or aural instructions back to the medical device 200, which can then pass the instructions on to a user via its user interface. Accordingly, the alarm system can remotely and in real-time instruct a rescuer with little or no medical training in the operation of the device and in the emergency treatment of the patient. In another embodiment, the alarm system can record data that is subsequently evaluated for quality control purposes.

The alarm system 100 and portable medical device 200 may exchange such information and instructions until the communication link 107 is terminated either by the device or the alarm system. For example, the medical device 200 and alarm system 100 can continue to exchange information and instructions until the medical device is deactivated (turned off), until emergency personnel arrive, for a predetermined time interval, etc. The method 700 then ends in a block 714.

Figure 8:
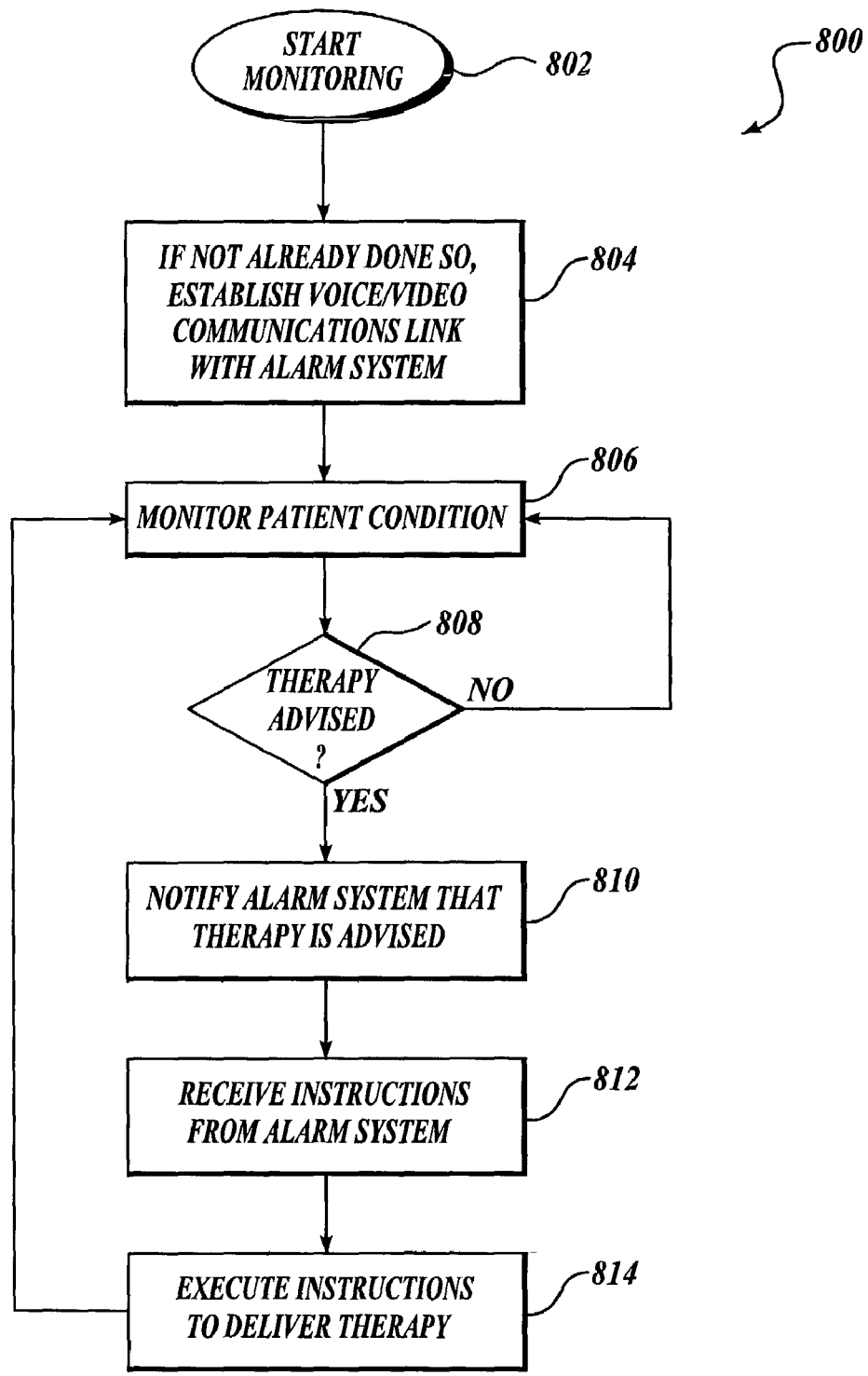
FIG. 8 is a flow diagram of a method by which a therapy-delivering, portable medical device and an alarm system communicate to provide instructions for delivering therapy during an emergency event.

It will be appreciated, however, that the medical device 200 and the alarm system 100 may communicate to provide specific monitoring of a patient's health condition and provide instructions for delivering therapy using the medical device. Accordingly, a method 800 by which a portable medical device 200 and an alarm system 100 communicate to provide such monitoring and instructions is shown in FIG. 8. Generally described, the method 800 may be embodied in a computer program executed by a portable emergency medical device 200 that instructs the medical device to notify the alarm system 100 of the emergency trigger event and exchange information related thereto. The method 800 begins in a block 802 and proceeds to block 804 in which a communications link capable of supporting audio and/or video communication is established with the alarm system 100, if such a communication link has not already been established. Once such a link has been established or if it has already been established, the method 800 proceeds to block 806 in which the condition of the patient is monitored by the medical device. It will be appreciated by those of ordinary skill in the art that it may be desirable to establish such a separate link if the original communication link does not support audio/video communication. However, this type of link is optional in that other embodiments of the present invention exist in which direct audio/video communication is not implemented.

As noted above, the portable medical device 200 may be of any type capable of delivering any one or combination of a variety of therapies for treatment of any one or combination of medical applications. For example, the portable medical device may be configured to monitor drug levels in a patient and deliver drug therapy accordingly. In another embodiment, the portable medical device is configured to analyze ECG data and delivery defibrillation therapy if a shockable rhythm is detected. Although these examples involve cardiac or drug therapy, monitoring and treatment of the patient's condition may involve other medical applications where a device can monitor or collect data from a patient, whether the data is monitored or collected by an automatic electronic sensor, such as an electrode or thermocouple, or whether the data is manually entered by the patient or the operator. In addition, treatment of the patient may involve delivery of CPR or other care instructions by the medical device.

Once monitoring begins, method 800 continues to decision block 808 where the portable medical device 200 determines if therapy for treating the patient's health condition is advised. Generally described, in this part of the process, the portable medical device 200 analyzes the patient data (monitored in block 806) and determines if the patient is experiencing an adverse health condition requiring therapy. For example, an adverse health condition may be a medical condition that is not in compliance with a prescription, such as a drug level reading from a patient that is not at a prescribed level, or a heart rate that is above or below a predetermined level. In another embodiment, the process of decision block 808 involves the analysis of ECG signals collected from the patient via a set of electrodes 205 connected to the portable medical device 200, when the device is an AED. Accordingly, if the portable medical device determines the presence of a predetermined health condition, e.g., shockable heart rhythm, the portable medical device may advise delivery of therapy, e.g., a therapeutic defibrillation shock. If therapy is advised, the medical device 200 notifies the alarm system 100 and transmits the detected health condition and any other pertinent data to the alarm system 100 via the communications link in block 810. In return, the portable medical device may receive further treatment and/or device operating instructions, including an instruction to delivery therapy from alarm system 100 in block 812. The device (or user thereto) then executes those instructions in block 814. The method then returns to block 806 so that the portable medical device may continue monitoring the patient.

In one embodiment of the present invention the medical device 200 delivers the advised therapy automatically upon receipt of instructions from the alarm system. However, in the other embodiments the medical device instructs the user to initiate the therapy delivery device (or initiates delivery itself without human intervention) immediately upon detection of a treatable condition rather than upon receipt of instructions from the alarm system 100. In yet another embodiment of the present invention, the portable medical device 200 communicates the monitored patient data to the alarm system 100 for analysis rather than analyze the data itself. More specifically, determining whether therapy is advisable in decision block 808 may also include transmitting the patient data to the alarm system 100 for storage and analysis. Accordingly, the logic of decision block 808 is actually carried out by the alarm system 100 and the results and corresponding instructions returned to the portable medical device 200. The device (upon instruction from the user or automatically) would then deliver therapy in accordance with the alarm system's instructions.

In yet another embodiment of the present invention, the portable medical device 200 may obtain patient-specific information from the alarm system 100 and use it to help monitor the patient's condition. More specifically, the portable medical device compares the data received from the alarm system to the patient data the device itself has monitored. For example, if the device is configured to detect abnormal heart rhythms, the device may use preexisting ECG data that is unique to the patient. Details of comparing ECG data is well known to those skilled in the art and, therefore, will not be described in further detail herein.

Returning to FIG. 8, if a predetermined health condition is not detected and thus, therapy is not advised in decision block 808, the method 800 returns to block 806 where monitoring of the patient continues.

Figure 9:
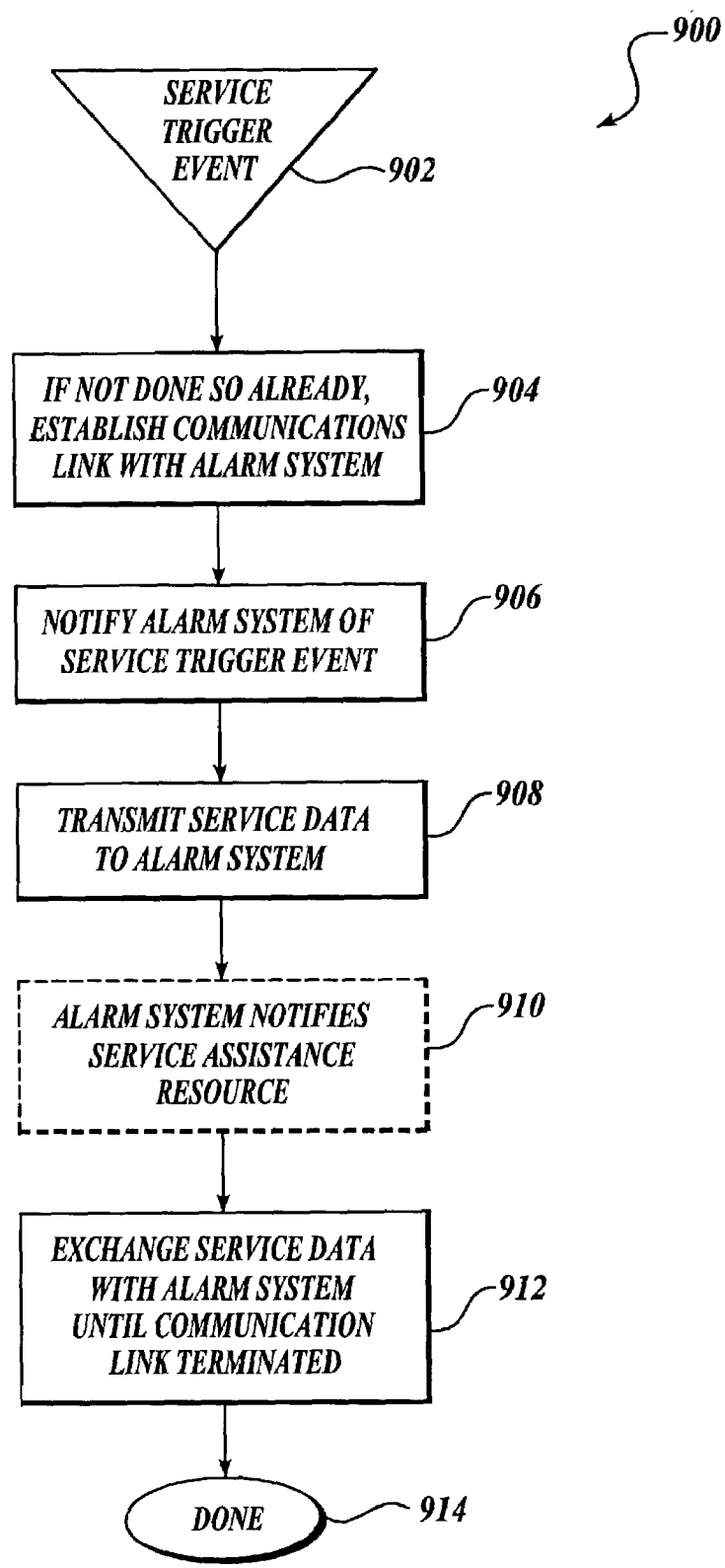
FIG. 9 is a flow diagram of a method by which a therapy-delivering, portable medical device triggers and communicates with an alarm system upon the occurrence of a service event.

As described above, trigger events may occur in a service context rather than an emergency context. Accordingly, FIG. 9 depicts a flow diagram of a method by which a portable medical device 200 triggers and communicates with an alarm system 100 upon the occurrence of a service trigger event. The method 900 begins at block 902 where a service trigger event occurs. As noted above, the service trigger event can be any one of a variety of events associated with the service status or maintenance of the portable medical device 200.

In response to the service trigger event, the method 900 continues to block 904 where the portable medical device establishes a communication link 107 with the alarm system 100. This allows the device and alarm system to communicate any patient, medical, location or device data to each other. As described above, the portable medical device may be configured to establish a bi-directional communication link with the alarm system sufficient for supporting a data, audio and/or video signal. It will be appreciated that in some embodiments of the present invention, it is possible that the communication link between the medical device 200 and the alarm system 100 may have already been established. For example, the medical device may be in constant communication with and/or continuously monitored by the alarm system 100 (much like a node in a computer network). Accordingly, separate establishment of the communication link may be unnecessary.

Next, the method 900 continues to block 906 where the portable medical device 200 notifies the alarm system 100 of the service trigger event via the communication link 107. It will be appreciated that the portable medical device will format and transmit the notification of the service trigger event in any form or format suitable for the alarm system. Once the alarm system has been notified of the trigger event, the portable medical device 200 may begin transmitting in block 908 any additional information or data regarding the trigger event. Such information may include, but is not limited to, self-test information, status information, software upgrade requests, service requests, etc. As shown in block 910 (which block is shown in phantom since this action is taken by the alarm system 100), upon receipt of the service trigger event notification from the medical device, the alarm system 100 may notify service resource assistance 150. Accordingly, the service resource assistance may dispatch service personnel or respond directly to the service trigger event. It will be appreciated that in lieu of notifying service assistance resources, it may be possible for the alarm system 100 itself to provide information and/or instructions to the portable medical device 200 relating to the service of the device.

Regardless of whether the alarm system further notifies an emergency assistance resource of the trigger event, the alarm system 100 and portable medical device 200 may exchange service data with one another until the communication link 107 is terminated in block 912. More specifically, once a communications link 107 has been established with alarm system 100 and the alarm system 100 has been notified of a service trigger event, the portable medical device 200 may continue transmitting data to the alarm system 100 and the alarm system may continue to respond. For example, if the medical device 200 requests a software upgrade, the alarm system 100 can download the upgrade directly to the device or request a field technician to provide the upgrade. The medical device 200 can then transmit confirmation of the upgrade to the alarm system 100, which in turn, may record such data for reporting purposes and/or send further information and/or instructions back to the medical device 200. Further, the alarm system 100 (or a user thereof) can send video, audio or textural instructions for use by the field technician back to the medical device 200, which can then pass the instructions on to a user via its user interface. Accordingly, the alarm system can remotely and in real-time monitor the condition or status of the device, thus saving valuable time and resources.

The alarm system 100 and portable medical device 200 may exchange such information and instructions until the communication link 107 is terminated. For example, the medical device 200 and alarm system 100 can continue to exchange information and instructions until the medical device is deactivated (turned off), until service personnel arrive, for a predetermined time interval, etc. The method 700 then ends in a block 914.

While the preferred embodiments of the invention have been illustrated and described, it will be appreciated that various changes can be made therein without departing from the scope of the invention. For instance, the above-described methods may be implemented in any of the above-described portable medical devices or the methods may be implemented in any other device capable of delivering therapy to a user. In addition, the portable medical devices may be embodied in any shape, size or form and may be configured to be internal to a person's body or operate as a wired or wireless stand-alone unit. Further the above-described methods may be implemented in any type of alarm system, whether the alarm system be fully automated or not.

The embodiments of the invention in which an exclusive property or privilege is claimed are defined as follows:

1. A method for communicating data directly between an alarm system and a portable medical device capable of delivering therapy, wherein the method comprises:
   determining the presence of a triggering event;
   establishing a direct communication link between the portable medical device capable of delivering therapy and the alarm system;
   communicating the triggering event and data related thereto between the portable medical device and the alarm system via the communication link; and
   initiating a response to the triggering event.

2. The method of claim 1, wherein the communication link between the portable medical device and the alarm system is established in response to determining the presence of the triggering event.

3. The method of claim 1, further comprising confirming that response to the triggering event has been initiated.

4. The method of claim 1, wherein the response to the triggering event is notifying an emergency service resource of the triggering event.

5. The method of claim 1, wherein the response to the triggering event is notifying an emergency service resource of the triggering event and the location of the portable medical device.

6. The method of claim 1, wherein the response to the triggering event is notifying a service assistance resource of the triggering event.

7. The method of claim 1, wherein the response to the triggering event is notifying a service resource of the triggering event and the location of the portable medical device.

8. The method of claim 1, further comprising communicating the location of the portable medical device between the portable medical device and the alarm system via the communication link.

9. The method of claim 1, wherein the communication link is configured to provide voice communication between a user of the portable medical device and a user located at an emergency assistance resource.

10. The method of claim 1, wherein the communication link between the portable medical device and the alarm system is a two-way communication link, wherein the two-way communication link is capable of communicating data, voice and video signals.

11. The method of claim 1, wherein the triggering event is related to an emergency.

12. The method of claim 11, wherein the emergency triggering event is an activation of the portable medical device.

13. The method of claim 11, wherein the emergency triggering event is deployment of the portable medical device.

14. The method of claim 11, wherein the emergency triggering event is based on a determination that the location of the portable medical device was changed, wherein the determination of the location change is provided by a location component that monitors data indicative of the geographical location of the portable medical device.

15. The method of claim 11, wherein the emergency triggering event is based on the presence of a predetermined medical condition of a user of the portable medical device.

16. The method of claim 15, wherein the predetermined medical condition is a discovery of an irregular heart condition of the user of the portable medical device.

17. The method of claim 15, wherein the predetermined medical condition is a discovery of a heart condition indicative of an arrhythmia.

18. The method of claim 1, further comprising:
   at the alarm system, receiving a signal indicative of a heartbeat pattern of the person from the portable medical device;
   storing the received heartbeat pattern signal;
   comparing one received heartbeat pattern signal to the stored heartbeat pattern signal to determine an irregular heartbeat pattern; and
   if an irregular heartbeat pattern is determined, producing a signal indicative of a triggering event.

19. The method of claim 1, wherein the response to the triggering event is an application of electric shock therapy to a patient coupled to the portable medical device.

20. The method of claim 11, wherein the emergency triggering event is the detection of an irregular level of medication applied to the user of the portable medical device.

21. The method of claim 1, wherein the response to the triggering event is an application of a dosage of medicine to the user of the portable medical device.

22. The method of claim 1, wherein the triggering event is related to servicing the portable medical device.

23. The method of claim 22, wherein the service triggering event is based on a determination that the portable medical device contains a failed component.

24. The method of claim 22, wherein the service triggering event is based on a determination that the portable medical device contains a component that is near expiration.

25. The method of claim 24, wherein the component near expiration is a software component configured for operating at least one component of the portable medical device.

26. The method of claim 22, wherein the service triggering event is based on a determination that a scheduled maintenance of the portable medical device is due.

27. The method of claim 1, wherein the portable medical device communicates the triggering event to the alarm system via the communication link.

28. The method of claim 1, wherein the alarm system communicates the triggering event to the portable medical device via the communication link.

29. A method for communicating data directly between an alarm system and a portable medical device capable of delivering therapy, wherein the method comprises:
   determining the presence of a triggering event;
   establishing a direct communication link between the portable medical device capable of delivering therapy and the alarm system, wherein the communication link is initiated by the portable medical device;
   notifying the alarm system of the triggering event via the communication link; and
   initiating a response to the triggering event.

30. The method of claim 29, further comprising transmitting location data from the portable medical device to the alarm system, wherein the location data describes the geographical location of the portable medical device.

31. The method of claim 29, wherein the triggering event is related to an emergency.

32. The method of claim 31, wherein the emergency triggering event is an activation of the portable medical device.

33. The method of claim 31, wherein the emergency triggering event is deployment of the portable medical device.

34. The method of claim 31, wherein the emergency triggering event is based on a determination that the location of the portable medical device was changed, wherein the determination of the location change is provided by a location component that monitors data indicative of the geographical location of the portable medical device.

35. The method of claim 31, wherein the emergency triggering event is based on the presence of a predetermined medical condition of a user of the portable medical device.

36. The method of claim 35, wherein the predetermined medical condition is a discovery of an irregular heart condition of the user of the portable medical device.

37. The method of claim 35, wherein the predetermined medical condition is a discovery of a heart condition indicative of an arrhythmia.

38. The method of claim 29, wherein the response to the triggering event is notifying an emergency service resource of the triggering event.

39. The method of claim 29, wherein the triggering event is related to servicing the portable medical device.

40. The method of claim 39, wherein the service triggering event is based on a determination that the portable medical device contains a failed component.

41. The method of claim 39, wherein the service triggering event is based on a determination that the portable medical device contains a component that is near expiration.

42. The method of claim 41, wherein the component near expiration is a software component configured for operating at least one component of the portable medical device.

43. The method of claim 41, wherein the service triggering event is based on a determination that a scheduled maintenance of the portable medical device is due.

44. The method of claim 29, wherein the triggering event is a request for a software upgrade and the response to the triggering event is a transmission of the software upgrade to the portable medical device.

45. The method of claim 29, wherein the triggering event is a request for user training.

46. The method of claim 29, wherein the response to the triggering event is notifying a service assistance resource of the triggering event.

47. A monitoring system, comprising:
a therapy-delivering, portable medical device having a communication interface; and
an alarm system having a communications interface for establishing a direct communications link with the communication interface of the portable medical device, wherein data describing a triggering event is communicated over the communications link, and wherein the alarm system is configured to provide a response to the triggering event.

48. The monitoring system of claim 47, further comprising a communications circuit configured to provide a communications link between the alarm system and a remote system of a service provider.

49. The monitoring system of claim 47, wherein the portable medical device is an automated external defibrillator.

50. The monitoring system of claim 47, wherein the portable medical device is configured to receive medical data that indicates a heart condition of a user.

51. The monitoring system of claim 47, wherein the portable medical device is configured to receive control signals from the alarm system, wherein the control signals apply electric shock therapy to a user of the portable medical device.

52. The monitoring system of claim 47, wherein the portable medical device further comprises a control unit configured to communicate data indicative of a health condition of a user, wherein the health condition is indicative of an amount of medication applied to the user.

53. The monitoring system of claim 47, wherein the data received and transmitted between the portable medical device and the alarm system communicates a signal that models a heartbeat of a user.

54. The monitoring system of claim 48, wherein the portable medical device comprises a control unit configured to provide two-way communication between the portable medical device and the remote system of the service provider.

55. The monitoring system of claim 47, wherein the portable medical device further comprises: a positioning circuit capable of generating data indicative of the geographic position of the portable medical device; and a communication circuit for communicating the data indicative of the geographic position of the portable medical device.

56. The monitoring system of claim 47, wherein the portable medical device and alarm system comprise a communications interface for providing bi-directional data and voice communications between a monitoring station of the alarm system.

57. The monitoring system of claim 47, further comprising a plurality of medical devices capable of delivering therapy, wherein the plurality of medical devices each comprise a circuit that is configured to detect a triggering event, wherein the circuit of the plurality of medical devices are configured to electronically communicate with the alarm system.

58. A method for communicating data related to a portable medical device capable of delivering therapy, wherein the method comprises:
determining the occurrence of a triggering event relating to the portable medical device;
establishing in response to the triggering event a direct first communication link between an alarm system and an assistance resource; and
transmitting an alarm signal between the alarm system and the assistance resource through the first communication link.

59. The method of claim 58, further comprising:
establishing a second communication link between the alarm system and the portable medical device; and
communicating the triggering event and data related thereto between the portable medical device and the alarm system through the second communication link.

60. The method of claim 58, wherein the alarm signal is generated in response to the triggering event.

61. The method of claim 58, wherein the triggering event is removal of the portable medical device from a location where the portable medical device resides when not in use.

62. The method of claim 58, wherein the triggering event is operation of the portable medical device.

63. The method of claim 58, wherein the triggering event is an emergency triggering event.

64. The method of claim 63, wherein the emergency triggering event is activation of the portable medical device.

65. The method of claim 63, wherein the emergency triggering event is deployment of the portable medical device.

66. The method of claim 63, wherein the emergency triggering event is based on a determination that the location of the portable medical device was changed, wherein the determination of the location change is provided by a location component that monitors data indicative of the geographical location of the portable medical device.

67. The method of claim 63, wherein the emergency triggering event is based on the presence of a predetermined medical condition of a user of the portable medical device.

68. The method of claim 67, wherein the predetermined medical condition is a discovery of an irregular heart condition of the user of the portable medical device.

69. The method of claim 67, wherein the predetermined medical condition is a discovery of a heart condition indicative of an arrhythmia.

70. The method of claim 63, wherein the emergency triggering event is the detection of an irregular level of medication applied to the user of the portable medical device.

71. The method of claim 58, wherein the triggering event is a service triggering event related to servicing the portable medical device.

72. The method of claim 71, wherein the service triggering event is based on a determination that the portable medical device contains a failed component.

73. The method of claim 71, wherein the service triggering event is based on a determination that the portable medical device contains a component that is near expiration.

74. The method of claim 73, wherein the component near expiration is a software component configured for operating at least one component of the portable medical device.

75. The method of claim 72, wherein the service triggering event is based on a determination that a scheduled maintenance of the portable medical device is due.

76. The method of claim 58, wherein upon determining the occurrence of the triggering event, a dosage of medicine is applied to a user of the portable medical device.

77. The method of claim 58, wherein upon determining the occurrence of the triggering event, an electric shock therapy is applied to the user coupled to the portable medical device.

78. The method of claim 58, wherein upon determining the occurrence of the triggering event, the assistance resource is notified of the location of the portable medical device.

79. The method of claim 58, wherein upon determining the occurrence of a triggering event, a service resource is notified of the triggering event and the location of the portable medical device.

80. The method of claim 59, further comprising communicating the location of the portable medical device between the portable medical device and the alarm system via the second communication link.

81. The method of claim 59, wherein the first and second communication links are configured to provide voice communication between a user of the portable medical device and a user located at the assistance resource.

82. The method of claim 59, wherein the first and second communication links are two-way communication links.

83. The method of claim 59, wherein the first and second communication links are capable of communicating data, voice and video signals.

84. The method of claim 58, further comprising:
at the alarm system, receiving a signal indicative of a normal heartbeat pattern of a person coupled to the portable medical device;
storing the received normal heartbeat pattern;
comparing a heartbeat pattern signal of a patient coupled by the portable medical device to the stored normal heartbeat pattern to determine an irregular heartbeat pattern; and
if an irregular heartbeat pattern is determined, producing a signal indicative of a triggering event.

85. The method of claim 58, wherein the assistance resource communicates the triggering event to the alarm system via the first communication link.

86. The method of claim 58, wherein the alarm system communicates the triggering event to the assistance resource via the first communication link.

87. An alarm system operable to communicate data between as assistance resource and an alarm system, the data related to a portable medical device capable of delivering therapy wherein the alarm system comprises:
means for determining the occurrence of a triggering event relating to the portable medical device;
means for establishing a direct first communication link with the assistance resource in response to the triggering event; and
means for transmitting an alarm signal to the assistance resource through the first communication link.

88. The alarm system of claim 87, further comprising:
means for establishing a second communication link with the portable medical device; and
means for communicating the triggering event and data related thereto between the portable medical device and the alarm system through the second communication link.

89. The alarm system of claim 87, wherein the triggering event comprises an emergency triggering event.

90. The alarm system of claim 87, wherein the triggering event comprises a service triggering event.

91. The alarm system of claim 87, further comprising means for instructing the portable medical device upon determining the occurrence of the triggering event.

92. The alarm system of claim 87, further comprising means for instructing the portable medical device to apply an electric shock to a user coupled to the portable medical device.

93. The alarm system of claim 87, further comprising means for notifying the assistance resource of the location of the portable medical device.

94. The alarm system of claim 87, further comprising means for notifying a service resource of the triggering event and the location of the portable medical device.

95. The alarm system of claim 87, further comprising means for receiving data indicating the location of the portable medical device via the second communication link.

96. The alarm system of claim 88, wherein the first and second communication links are configured to provide voice communication between a user of the portable medical device and a user located at the assistance resource.

97. The alarm system of claim 88, wherein the first and second communication links are two-way communication links.

98. The alarm system of claim 88, wherein the first and second communication links are capable of communicating data, voice and video signals.

99. The alarm system of claim 87, further comprising:
means for receiving a signal indicative of a normal heartbeat pattern of a person coupled to the portable medical device;
means for sorting the received normal heartbeat pattern;
means for comparing a heartbeat pattern signal of a patient coupled to the portable medical device to the stored normal heartbeat pattern to determine an irregular heartbeat pattern; and
means for producing a signal indicative of a triggering event if an irregular heartbeat pattern is determined.

100. The alarm system of claim 87, further including means for transmitting the triggering event and data related thereto to the assistance resource via the first communication link.

101. The method of claim 87, further including means for receiving communication of the occurrence of a triggering event and data related thereto from the assistance resource via the first communication link.

* * * * *

UNITED STATES PATENT AND TRADEMARK OFFICE
CERTIFICATE OF CORRECTION

PATENT NO.       : 7,120,488 B2                                   Page 1 of 1
APPLICATION NO.  : 10/141574
DATED            : October 10, 2006
INVENTOR(S)      : Richard C. Nova et al.

It is certified that error appears in the above-identified patent and that said Letters Patent is hereby corrected as shown below:

In column 22, line 7, in Claim 84, delete "by" and insert -- to --, therefor.

In column 22, line(s) 42-43, in Claim 91, delete "upon determining the occurrence of the triggering event." and
insert -- to apply a dosage of medicine to a user of the portable medical device upon determining the occurrence of the triggering event. --, therefor.

In column 23, line 5, in Claim 99, delete "sorting" and insert -- storing --, therefor.

Signed and Sealed this

Seventeenth Day of August, 2010

David J. Kappos
*Director of the United States Patent and Trademark Office*